United States Patent [19]
Dashevsky et al.

[11] Patent Number: 5,833,886
[45] Date of Patent: Nov. 10, 1998

[54] THERMOSTABILITY ENHANCEMENT OF POLYPHOSPHATE FLAME RETARDANTS

[75] Inventors: Sophia Dashevsky, Fair Lawn, N.J.; Danielle A. Bright, New City, N.Y.

[73] Assignee: Akzo Nobel NV, Arnhem, Netherlands

[21] Appl. No.: 932,320

[22] Filed: Sep. 17, 1997

[51] Int. Cl.⁶ ............................. C08K 5/52; C08K 5/51; C09K 21/00
[52] U.S. Cl. .................... 252/601; 252/609; 524/127; 524/128
[58] Field of Search ................. 524/127, 128; 252/601, 609

[56] References Cited

U.S. PATENT DOCUMENTS

| | | | |
|---|---|---|---|
| 3,697,463 | 10/1972 | Oakes et al. | 524/128 |
| 4,083,789 | 4/1978 | Morgan et al. | 252/601 |
| 5,508,462 | 4/1996 | Bright et al. | 558/99 |
| 5,521,236 | 5/1996 | Moy et al. | 524/101 |
| 5,618,867 | 4/1997 | Bright et al. | 524/127 |
| 5,627,228 | 5/1997 | Kobayashi et al. | 524/127 |
| 5,679,288 | 10/1997 | Kim et al. | 252/609 |

FOREIGN PATENT DOCUMENTS

| | | | |
|---|---|---|---|
| 521628 | 1/1993 | European Pat. Off. | C07F 9/12 |
| 64-223158 | 9/1989 | Japan | C08L 71/04 |
| 2187456 | 7/1990 | Japan . | |

*Primary Examiner*—C. H. Kelly
*Attorney, Agent, or Firm*—Richard P. Fennelly

[57] ABSTRACT

The thermostability of an aromatic polyphosphate composition an be improved by the addition of an effective amount of a hydroxy-terminated aromatic polyphosphate composition for such.

8 Claims, No Drawings

THERMOSTABILITY ENHANCEMENT OF POLYPHOSPHATE FLAME RETARDANTS

BACKGROUND OF THE INVENTION

The term "polyphosphate" as used herein is intended to mean a composition of the type to be described in more detail below which contains two or more phosphate moieties in its structure. Aromatic polyphosphate compositions which can be predominantly diphosphate in nature or of higher molecular weight (i.e., oligomeric) and which are not hydroxy-terminated are known to persons of ordinary skill in the art with representative examples being described in European Patent Publication Nos. 509,506 and 521,628 and Japanese Patent Publication No. 227,632/1988. A general formula which can be used to represent compositions of this type is the following:

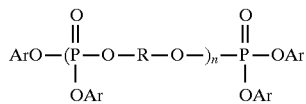

with Ar being aryl, such as unsubstituted phenyl, R being a hydrocarbyl group such as phenyl, diphenyl, 4,4'-isopropylidenediphenyl, and the like (with a particularly preferred diol being resorcinol) and with n ranging from 1 to about 10. Mixtures where n is a decimal number are also contemplated. An example of a commercially available material of this type containing a bridging group derived from resorcinol is available under the trademark FYROLFLEX® RDP from Akzo Nobel Chemicals Inc.

Hydroxy-terminated aromatic polyphosphate compositions are also known in the art. For example, an oligomeric phosphate is depicted as one of the products formed by the processes described in Japanese Patent Publication No. 223,158/1989. The product that is desired is a mixture of 22%–65%, by weight, of a reactive, hydroxy-terminated monophosphate ester, 15%–30% of a non-reactive, non-hydroxy-terminated phosphate ester, and 5%–63% of the hydroxy-terminated oligomeric phosphate ester. More recent U.S. Pat. No. 5,508,462 to D. A. Bright et al. describes and claims a process for making certain hydroxy-terminated aromatic polyphosphate compositions.

SUMMARY OF THE INVENTION

The present invention relates to a fluid flame retardant composition which comprises an aromatic polyphosphate composition and an effective amount of a hydroxy-terminated aromatic polyphosphate compositions for improvement of the thermostability thereof.

DESCRIPTION OF THE PREFERRED EMBODIMENTS

It has now been found that a hydroxy-terminated aromatic polyphosphate is an effective thermostability enhancing agent in the aforementioned type of aromatic polyphosphate composition which is not hydroxy-terminated. In general terms, the aromatic polyphosphate composition which is not hydroxy-terminated will be present in major amount in the composition (e.g., from about 99% to about 51%, by weight of the composition, preferably from about 90% to about 70%, by weight of the composition).

The desired hydroxy-terminated aromatic polyphosphate product is of the formula:

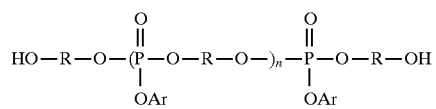

with Ar and R being defined as given above, and with n ranging from about 1 to about 20. U.S. Pat. No. 5,508,462 to D. A. Bright et al. is incorporated herein by reference to illustrate how such a hydroxy-terminated aromatic polyphosphate composition can be formed.

The present invention is illustrated by the Examples which follow.

EXAMPLES

Varying amounts of an oligomeric resorcinol-based polyphosphate flame retardant (available under the trademark FYROLFLEX® RDP from Akzo Nobel Chemicals Inc.) and the analogous hydroxy-terminated composition described and claimed in U.S. Pat. No. 5,508,462 were mixed together by solution blending in the amounts indicated in the Table set forth below (i.e., 20 wt %, 50 wt %, and 80 wt % of the hydroxy-terminated composition. The thermostability of the blends were tested at the temperatures also given in the table using a PERKIN ELMER TGA-7 thermogravimetric analyzer, in air, at a heating rate of 10° C. per minute. The effect of blending the various amounts of the hydroxy-terminated composition were determined as an increase in retained weight for the system at the given temperature. The data given in the Table sets forth three, sequential numerical values when the hydroxy-terminated composition was present in the blends that were tested: the actual determination of the percentage of original bisphosphate material that was retained after the thermogravimetric analysis; the expected retained weight of bisphosphate that was calculated using the rule of mixtures; and the percentage increase for the experimental retained weight value as compared to the calculated value:

| Temp. (°C.) | Retained Weight of Blends* (%) | | | | |
|---|---|---|---|---|---|
| | 100/0* | 80/20 | 50/50 | 20/80 | 0/100 |
| 400 | 54 | 70/59/19** | 77/65/18 | 75/72/4 | 77 |
| 460 | 14 | 44/26/70 | 63/38/66 | 70/60/17 | 72 |
| 500 | 4.3 | 35/17/106 | 57/37/54 | 67/57/18 | 70 |
| 560 | 3.5 | 31/15/107 | 48/33/45 | 58/50/16 | 62 |
| 600 | 3.0 | 29/14/107 | 44/30/47 | 53/46/15 | 57 |
| 700 | 1.4 | 21/10/110 | 31/23/35 | 39/37/5 | 44 |
| 780 | 0.2 | 15/7/114 | 22/17/29 | 22/17/29 | 34 |

*the weight ratio of the FYROLFLEX ® RDP brand polyphosphate flame retardant to the hydroxy-terminated polyphosphate component.
**the first number gives the wt % residue, experimental; the second number gives the wt % residue, calculated; and the third number gives the % increase in residue comparing the experimental value to the calculated value.

The data indicate that the addition of the hydroxy-terminated composition to the FYROLFLEX® RDP brand polyphosphate flame retardant enhanced the thermostability of that product and that the weight loss of the resulting product blend was thereby reduced. All of the blends showed a higher residual weight over calculated values. The most pronounced effect was noted for the blend containing 20 wt % of the hydroxy-terminated composition. At 500° C., the blend produced a 35 wt % residue, giving a 106% increase, as compared to the expected 17 wt % residue expected from the 80% contribution of the neat FYROLFLEX® RDP brand polyphosphate flame retardant (a baseline 4.3 wt % residue value for the neat material) added to the 20% contribution from the hydroxy-terminated composition (a baseline 70 wt % residue value for the neat material). As a result the volatility of the FYROLFLEX® RDP brand polyphosphate flame retardant was substantially reduced and its decomposition is at least partially shifted to the condensed phase.

The foregoing Examples are provided to illustrate certain embodiments of the present invention and, for that reason, should not be construed in a limiting sense. The scope of protection sought is set forth in the claims which follow.

We claim:

1. A fluid flame retardant composition which comprises an aromatic polyphosphate composition and an effective amount of a hydroxy-terminated aromatic polyphosphate composition for improvement of the thermostability thereof.

2. A composition as claimed in claim 1 wherein the flame retardant composition comprises a major amount of an aromatic polyphosphate composition of the formula

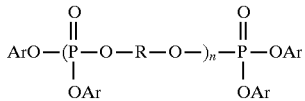

with Ar being aryl, R being a hydrocarbyl group, and with n ranging from 1 to about 10.

3. A composition as claimed in claim 1 wherein the hydroxy-terminated aromatic polyphosphate composition is of the formula:

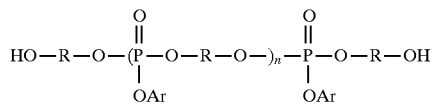

with Ar being aryl, R being a hydrocarbyl group, and with n ranging from 1 to about 20.

4. A composition as claimed in claim 1 wherein the flame retardant composition comprises a major amount of an aromatic polyphosphate composition of the formula

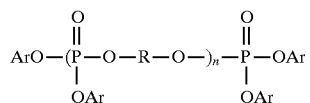

with Ar being aryl, R being a hydrocarbyl group, and with n ranging from 1 to about 10 and wherein the hydroxy-terminated aromatic polyphosphate composition is of the formula:

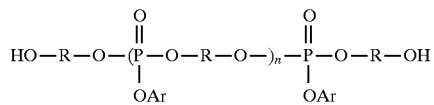

with Ar being aryl, R being a hydrocarbyl group, and with n ranging from 1 to about 20.

5. A composition as claimed in claim 1 wherein the aromatic polyphosphate composition comprises from about 99% to about 51%, by weight of the composition.

6. A composition as claimed in claim 2 wherein the aromatic polyphosphate composition comprises from about 99% to about 51%, by weight of the composition.

7. A composition as claimed in claim 3 wherein the aromatic polyphosphate composition comprises from about 99% to about 51%, by weight of the composition.

8. A composition as claimed in claim 4 wherein the aromatic polyphosphate composition comprises from about 99% to about 51%, by weight of the composition.

* * * * *